(12) United States Patent
Mosbach et al.

(10) Patent No.: US 6,316,235 B1
(45) Date of Patent: Nov. 13, 2001

(54) PREPARATION AND USE OF MAGNETICALLY SUSCEPTIBLE POLYMER PARTICLES

(75) Inventors: Klaus Mosbach, Furulund; Dario Kriz, Bgärred; Richard J. Ansell, Lund, all of (SE)

(73) Assignee: IGEN, Inc., Gaithersburg, MD (US)

( * ) Notice: Subject to any disclaimer, the term of this patent is extended or adjusted under 35 U.S.C. 154(b) by 0 days.

(21) Appl. No.: 09/480,637

(22) Filed: Jan. 10, 2000

Related U.S. Application Data

(63) Continuation of application No. 08/531,503, filed on Sep. 21, 1995, now abandoned, which is a continuation-in-part of application No. 08/517,493, filed on Aug. 21, 1995, now abandoned, which is a continuation-in-part of application No. 08/451,711, filed on May 26, 1995, now abandoned.

(51) Int. Cl.$^7$ ............................. C12N 11/08; B03C 1/02; G01N 33/545; H01F 1/01
(52) U.S. Cl. ............................. 435/180; 209/8; 210/222; 252/62.51 R; 435/176; 435/180; 435/280; 436/525; 436/531; 526/95
(58) Field of Search ................................... 435/174, 176, 435/177, 180, 182, 280; 210/222; 209/8; 436/525, 531; 252/63.51 R; 526/95

(56) References Cited

U.S. PATENT DOCUMENTS

| | | | |
|---|---|---|---|
| 3,970,518 | * 7/1976 | Giaever | 435/239 |
| 3,985,649 | * 10/1976 | Eddelman | 210/695 |
| 4,106,488 | * 8/1978 | Gordon | 424/1.37 |
| 4,115,534 | * 9/1978 | Ithakissios | 436/500 |
| 4,335,094 | * 6/1982 | Mosbach | 424/1 |
| 5,418,151 | * 5/1995 | Goodhue et al. | 435/105 |

FOREIGN PATENT DOCUMENTS

8604087 * 7/1986 (WO).

OTHER PUBLICATIONS

Kempe, Marie, Chiral Recognition, Doctoral Dissertation, Department of Pure and Applied Biochemistry, University of Lund, Sweden, pp. 1–77 (1994).*

Andersson, et. al., Bioseparation and Catlaysis in Molecularly Imprinted Polymers. Molecular Interactions in Bioseparations, pp. 383–394 (1993).*

Wulff, et. al., J. Org. Chem., vol. 56, No. 1, pp. 395–400 (1991).*

Wulff, Gunter, The Role of Binding–Site Interactions in the Molecular Imprinting of Polymers, Eisevier Science Publishers, pp. 85–87 (1993).*

* cited by examiner

*Primary Examiner*—David M. Naff
(74) *Attorney, Agent, or Firm*—Morgan & Finnegan, LLP

(57) ABSTRACT

Polymer particles are formed containing molecular memory recognition sites and magnetically susceptible components. The particles are prepared by co-polymerizing one or more monomers and a cross-linking agent in the presence of at least one imprint molecule and at least one magnetically susceptible component such as iron oxide or nickel oxide, and removing the imprint molecule to form molecular memory recognition sites. The particles are also prepared by co-polymerizing the monomer and cross-linking agent in the presence of the imprint molecule to produce particles, removing the imprint molecule and associating magnetically susceptible components with the particles. The particles may also be prepared containing selective adsorbents such as cells or antibodies. The particles are used for selective adsorption of a product such as separating and resolving two different enantiomeric forms due to one of the forms adsorbing to a memory recognition site created by using the form as an imprint molecule. A magnetic field is used to separate particles containing an adsorbed product from a solution in which the product is adsorbed to the particles.

12 Claims, 6 Drawing Sheets

PREPARATION AND USE OF MAGNETICALLY SUSCEPTIBLE POLYMER PARTICLES

CROSS-REFERENCES TO RELATED APPLICATIONS

This application is a continuation of application Ser. No. 08/531,503, filed Sep. 21, 1995, now abandoned, which is a continuation-in-part of application Ser. No. 08/517,493, filed Aug. 21, 1995, now abandoned, and a continuation-in-part of application Ser. No. 08/451,711, filed May 26, 1995, now abandoned. The present application incorporates by reference the entire contents of each of these prior applications.

FIELD OF THE INVENTION

The present invention is broadly directed to magnetically susceptible polymer particles having specifically-tailored adsorptivities and to related processes. The invention also encompasses the related processes:

(i) for making the particles;
(ii) for separating target compounds from other compounds using the particles; and
(iii) for delivering selected compounds to targeted areas of concentration using the particles.

Of particular interest are particles and processes that involve biologically active substances, e.g., pharmaceuticals.

BACKGROUND OF THE INVENTION

In describing the invention along with the background thereof, certain documents are either explicitly discussed or are relevant sources of background information. These documents are indicated by number (e.g. "document 1") throughout the remainder of the specification and are identified immediately prior to the claims. The present application incorporates by reference the entire contents of each of these documents.

Biologically active substances are often produced in relatively small quantities in processes wherein the desired final product is frequently in the presence of other, perhaps numerous, undesired compounds, mixtures, etc. The cost in terms of time, money, or equipment of isolating and/or purifying the desired product from the undesired product can be very significant. The cost for these post-production processes is ultimately borne by the purchaser of the desired product. As such, there is a continuing need in the art for materials and/or processes that improve the isolation and/or purification of compounds produced by biotechnological processes.

Existing isolation and/or purification techniques may include: (i) multistep bulk processes such as fractional crystallization; distillation, etc; or (ii) reactant conditions designed to produce only the desired product. The disadvantages of the techniques of (i) include relativity complicated processing and possible purification problems. The disadvantages of the techniques of (ii) include the high costs of obtaining such reactant conditions. For example, by using only particular enantiomers of particular reactants, it is possible to obtain a relatively high degree of purity in a desired chiral product (i.e., a unique enantiomer of the desired product). However, this process necessitates controlling the exact stereochemistry of all of the individual reactions which culminate in the formation of the desired enantiomeric product. This stereochemically control requires the use of particular enantiomeric forms of all the reactant compounds and is accordingly relatively expensive as compared to running reactions without using enantiomerically-pure compounds.

As will be apparent to those workers of ordinary skill in the art, the present invention directed to magnetically susceptible polymer particles having specifically-tailored adsorptivities and to processes employing such particles represents a patentable advance in the art and offers advantages over existing techniques.

SUMMARY OF THE INVENTION

The present invention is directed to magnetically susceptible polymer particles wherein the polymeric core of the particles has both specifically-tailored adsorptivities and magnetically susceptible components. Alternative embodiments of the present invention include the following related processes:

(i) for making the particles;
(ii) for separating target compounds from other compounds using the particles; and
(iii) for delivering selected compounds to targeted areas of concentration using the particles.

The selective adsorptivities of the particles arise from a combination of selective adsorbents and/or from molecular memory recognition sites (typically from molecular imprinting polymerization reactions). The particles are magnetically susceptible because of the presence of magnetically susceptible components such as metal oxides in intimate proximity to the polymeric core of the particles.

DETAILED DESCRIPTION OF THE INVENTION

The present invention is broadly directed to magnetically susceptible polymer particles with a polymeric core having specifically-tailored adsorptivities and magnetically susceptible components. Related processes of making such particles and separating and/or delivering compounds using the particles are also within the ambit of the present invention. Features of the invention include the following:

(i) the magnetic susceptibility of the particles;
(ii) the polymeric core of the particles;
(iii) the specifically-tailored adsorptivties of the particles;
(iv) making the particles; and
(v) separating and/or delivering compounds using the particles.

Each of these five noted features of the invention is individually explained at length below.

(i) The Magnetic Susceptibility.

The magnetic properties of the particles of the present invention offer several advantages as compared to nonmagnetic particles. In particular, the ability of the particles to be movably attracted to an area based upon magnetic forces of attraction provides an excellent basis for separating the particles from the surrounding chemical and physical environment.

Figure 2:
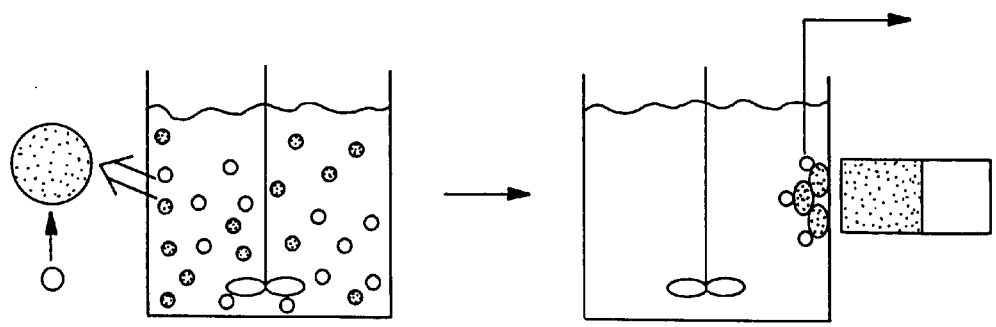
FIG. 2 schematically depicts a process for separating products using particles.

FIG. 2 schematically depicts a process for separating products using this magnetic ability of the particles. The left side of FIG. 2 illustrates the selective adsorption of desired products, originally distributed within a solution, onto the particles of the present invention. Before the application of a magnetic field, the adsorption process alone results in the particles being distributed thoughout the bulk solution and having adsorbed thereonto the desired products. The right portion of FIG. 2 illustrates the separation of these particles from the bulk solution due to the presence of a magnetic source located proximate to the bulk solution but yet outside of and not immersed within the solution. The magnet is represented by a horizontally-orientated rectangle divided into two sides of opposite polarity while the localization of the particles in the solution to the environment closest to the magnet is represented by the irregularly shaped dark area opposite the external magnet. In direct contrast to the situation shown in the left side, the particles in the right side are not distributed throughout the bulk solution. The localized particles in the right side are readily available for separation by e.g., (i) decanting off the bulk solution; (ii) lifting the particles out of the solution; and (iii) other appropriate techniques. The physical separation of the localized particles from the solution is shown by the up-and-to-the-right arrow along the inner right side of the container.

FIG. 2 thus represents four distinct processes as detailed below:

(i) The process of biotechnologically making a desired product (open circles). This is indicated by the depicted stirrer bar immersed at the central bottom portion of the bulk solution.
(ii) The process of adsorbing from the bulk solution onto the particles (closed circles) the desired products (open circles). This is illustrated at the far left side of FIG. 2 where the desired product is moving to come in contact with a particle.
(iii) The process of locating the particles (having a desired product already adsorbed thereonto) from the bulk solution into a much smaller area of solution by the imposition of a magnetic field created by an externally located magnet.
(iv) The process of physically separating the localized particles from the bulk solution. The noted up-and-to-the-right arrow represents this physical separation.

A first distinct advantage is that separation processes based upon the particles' magnetic susceptibility do not usually interfere with the actual biotechnological production of desired products. This is because the attractive magnetic forces used in such separations do not appreciably impact the reactions required to produce desired products.

A second distinct advantage of the particles of the present invention is that, although they are magnetically susceptible in the presence of a magnetic field, the particles themselves are not permanently magnetized. Rather, the particles contain magnetically susceptible components that will respond to the application of an applied magnetic field by temporarility exhibiting a magnetic orientation. It is this temporary magnetic orientation of the magnetically susceptible components that results in the particles' ability to be attracted to a magnet. Unlike a permanent magnet however, this magnetic orientation of the components is only temporary and it ceases upon the removal of the components from the exposure to and influence of the magnetic field. Because the particles of the present invention exhibit the described magnetic susceptibility without actually being permanently-magnetized, problems with particles magnetically combining together in the bulk solution are effectively prevented.

The particles of the present invention can be made magnetically susceptible in a variety of different processes. Five specific processes of imparting magnetic susceptibility to the particles are explained below. The first two processes at (a) can be viewed as pre-polymerization magnetization schemes while the last three processes at (b) can be viewed as post-polymerization magnetization schemes.

(a) Pre-Polymerization Magnetization.

Pre-polymerization magnetization entails the simultaneous (i) formation of the particles via polymerization; and (ii) incorporation into the then-forming particles of magnetically susceptible components.

Certain aspects of molecular imprinting polymerization reactions have been detailed in the literature as shown by the cited documents. However, a brief review of molecular imprinting techniques is provided here for the convenience of the reader.

Figure 1:
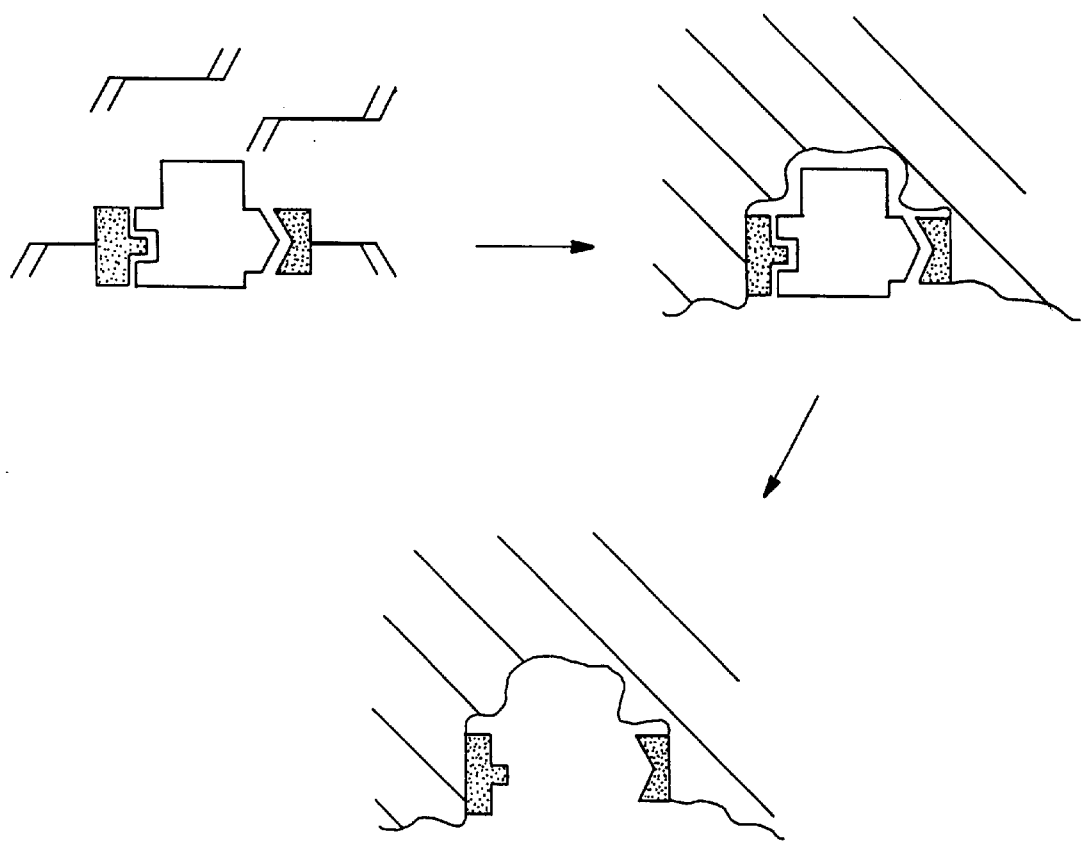
FIG. 1 schematically depicts a molecular imprinting polymerization reaction.

FIG. 1 schematically represents the preparation of molecularly imprinted particles having molecular memory recognition sites corresponding to the imprint molecule used in the polymerization reactions. Turning specifically to FIG. 1, the following is noted. First, in the upper left portion, there are are shown three different reactant monomers (one of them is shown twice). These monomers represent an operative combination of reactant functional monomers and reactant crosslinking monomers. The imprint molecule is the irregularly shaped molecule whose shape is closely matched at its left and right ends by two different reactant monomers. The actual polymerization reaction is represented by the upper right portion of FIG. 1. Here, the polymer has been formed and, at this time, it still contains the imprint molecule about which the polymerization occured. And finally, at the lower central portion of FIG. 1. the imprint molecule has now been removed from the polymer. At this point, the polymer will exhibit specifically-tailored adsorptivities for the imprint molecule that was originally present during the molecular imprinting polymerization reactions that formed this polymer.

Figure 3:
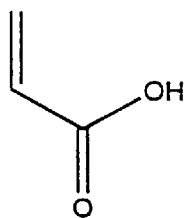
FIG. 3 depicts the chemical structures of twelve different reactant monomers capable of acting as functional monomers in non-covalent molecular imprinting polymerizations.
Figure 3:
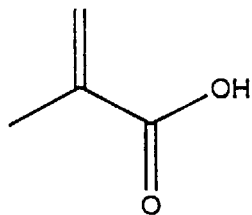
Figure 3:
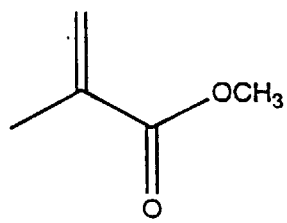
Figure 3:
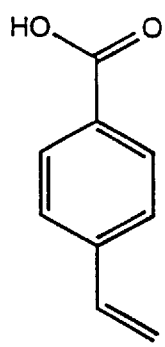
Figure 3:
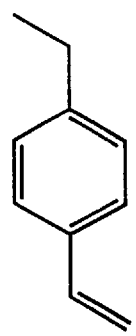
Figure 3:
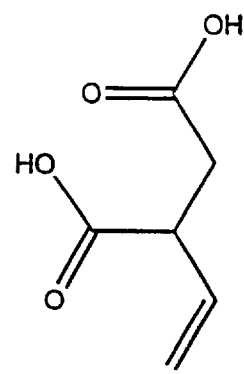
Figure 3:
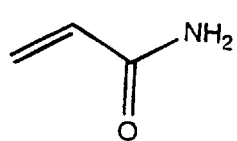
Figure 3:
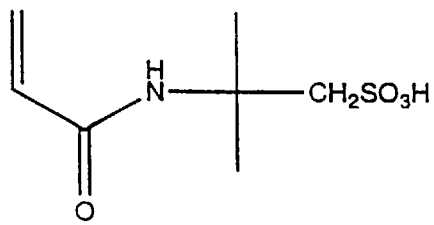
Figure 3:
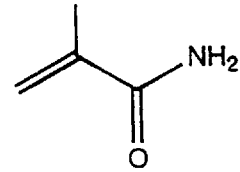
Figure 3:
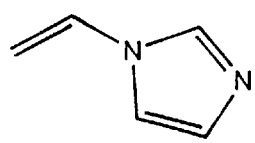
Figure 3:
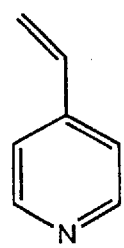
Figure 3:
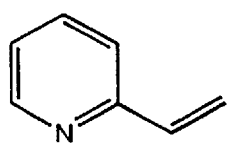
Figure 4:
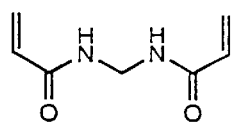
FIG. 4 depicts the chemical structures eleven different reactant monomers capable of acting as crosslinking monomers in non-covalent molecular imprinting polymerizations.
Figure 4:
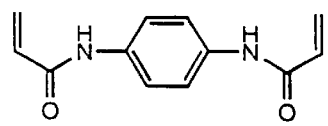
Figure 4:
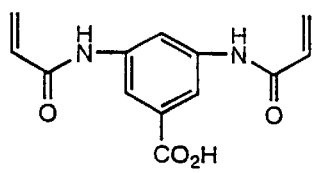
Figure 4:
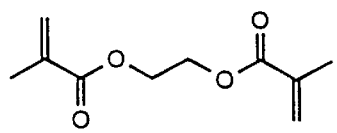
Figure 4:
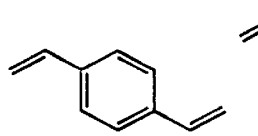
Figure 4:
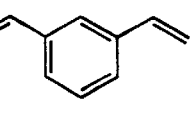
Figure 4:
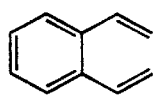
Figure 4:
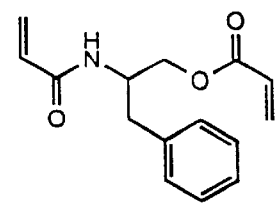
Figure 4:
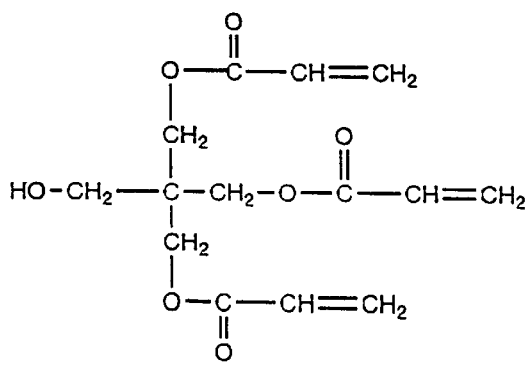
Figure 4:
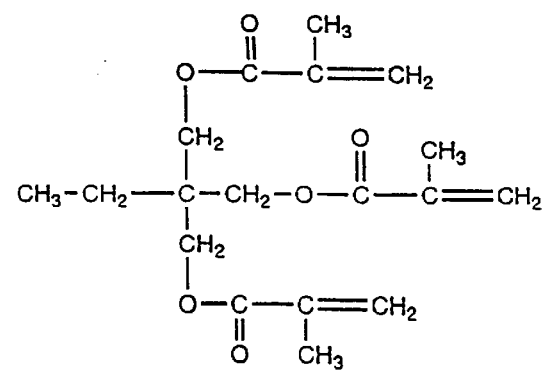
Figure 4:
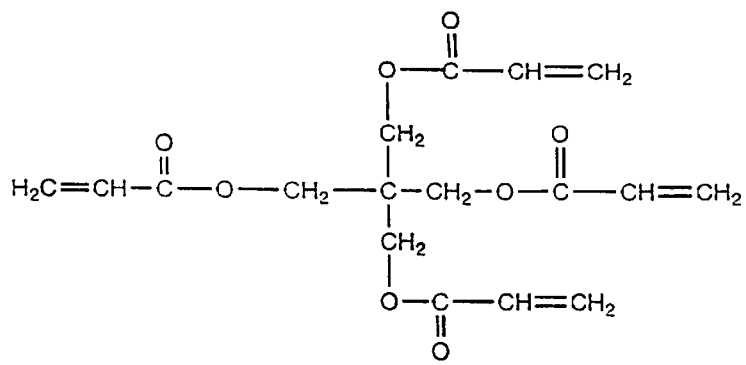
Figure 5:
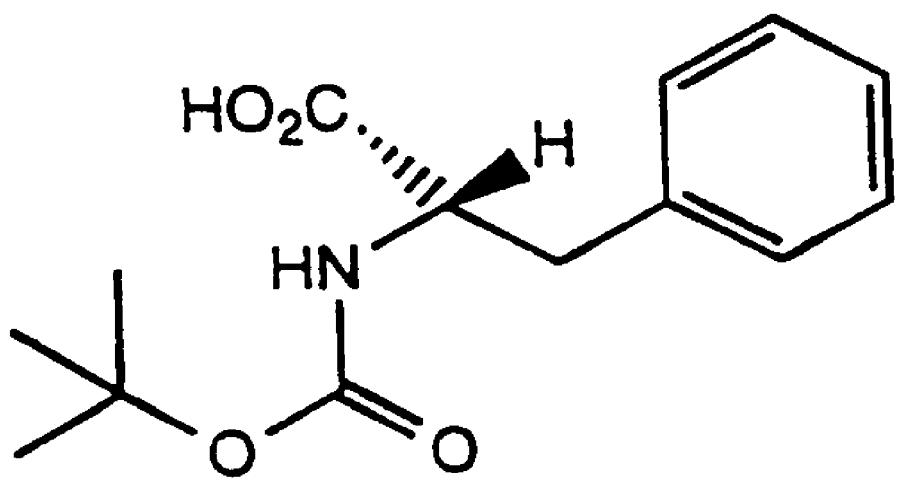
FIG. 5 depicts the stereochemically structure of t-butoxycarbonly-L-phenylalanine including the chiral arrangement of the asymmetric carbon directly bonded to the nitrogen atom.

The reactant monomers suitable for use in the molecular imprinting techniques of the present invention include functional monomers and crosslinking monomers. The chemical structures of twelve different functional monomers is shown in FIG. 3. The chemical structures of eleven different crosslinking monomers is shown in FIG. 4.

Returning to the discussion of the magnetically susceptible components of the particles, the first two pre-polymerization magnetization processes for making the particles use the above-described molecular imprinting polymerization reactions in the presence of magnetically susceptible components. These components are somehow entrapped within the growing polymer matrix and the resulting particles are themselves magnetically susceptible.

Two types of these components are metal oxides and ferrofluids. Each of these components is being used in a patentable fashion in the present invention. Thus, the first pre-polymerization magnetization process for producing magnetically susceptible imprinted polymer particles of the present invention uses molecular imprinting polymerization wherein metal oxides are disposed within the same solution containing the reactant monomers. Analagously, the second process uses molecular imprinting polymerization wherein ferrofluids are disposed within the same solution containing the reactant monomers.

For each of these above two-processes particular reference is made to the disclosure of document 13.

(b) Post-Polymerization Magnetization.

Post-polymerization reaction entails (i) first, the formation of the molecularly imprinted particles (not magnetically susceptible at this time); and (ii) subsequently, the association of magnetically susceptible components with these particles to thereby confer the sought-for magnetic susceptibility upon the particles.

The third magnetization process is direct chemical precipitation from solution onto the polymer particles of magnetically susceptible components such as metal oxides. Example 2 details the experimental preparation of magnetically susceptible polymer particles of the present invention using this direct chemical precipitation method.

The fourth and fifth magnetization processes use physical entrapment within the pores of the particles of magnetically susceptible components. In particular, running a solution containing magnetically susceptible components in the form of (i) either metal oxides [the fourth process] or (ii) ferrofluids [the fifth process] over the particles can result in such entrapment-processes whereby, after sufficient exposure, the particles will be imbued with sufficient quantities of the magnetically susceptible components from the running solution that they will themselves become magnetically susceptible. Once again, particular reference is made to the incorporated documents for some of the details of molecular imprinting techniques.

(ii) The Polymeric Core.

The polymeric core of the particles of the present invention is simply an alternative expression for the resulting polymer that reflects the fact that the particles are approximately spherical or spherical-like in shape. The polymer core comprises the resulting polymer from the molecular imprinting polymerization reactions.

The polymer core need not be uniform throughout. In particular, the present invention can be considered to include polymer cores that completely surround other material. The other material might be any of the following things: organic; inorganic, including metals and/or colloidal metals, or any other material that does not detrimentally interfere with the specifically-tailored adsorptivities or magnetic susceptibilities of the particles of the present invention.

(iii) Tile Specifically-Tailored Adsorptivities.

The specifically-tailored adsorptivities of the particles can arise from a combination of selective adsorbents associated with the particles or molecular memory recognition sites associated with the particles.

The manner in which selective adsorbents can be associated with the particles of the present invention will be apparent to those of ordinary skill.

The recognition sites originate from molecular imprinting polymerization reactions. The reader is referred to the incorporated documents for certain details of these recognition sites. Example 1, however, proves explicit experimental verification of the operability of the separating and resolving of two enantiomers of an optically active chiral compound using a chromatography column and particles of the present invention. A detailed description of optical activity is presented in document 12.

(iv) Making, the Particles.

Example 1 details an experimental procedure for making particles of the present invention using the suspension/perfluorocarbon technique described in document 13 and the pre-polymerization magnetization process with magnetic iron oxides.

Example 2 details an experimental procedure for making particles of the present invention using the post-polymerization magnetization direct chemical precipitation process with a mixture of iron (II) chloride and iron (III) chloride in the presence of ammonium hydroxide.

The disclosure herein is sufficiently detailed, in combination with the incorporated documents, to enable one of ordinary skill to prepare particles encompassed by the present invention.

(v) Separating and/or Delivering Compounds.

Example 1 provides experimental details of the process of separating and resolving two different enantiomeric forms of t-butoxycarbonyl-(D/L)-phenylalanine using particles of the present invention in a chromatography column.

The skilled artisan would clearly be enabled of other processes within the ambit of the present invention. In particular, a skilled worker would be able to perform the following processes with the particles of the present invention:

1 isolating desired products in situ as they are formed;
2 delivering compounds to areas targeted by the application of a magnetic field in that area; and
3 concentrating within an organism compounds to areas targeted by the application of a magnetic field in that area.

Although the above-description of the invention provides an enabling disclosure to the skilled artisan. applicants additionally provide the following specific examples of the embodiments of this invention. These examples are provided for the convenience of the reader and are in no way intended to be limiting with respect to the interpretation of the appended claims.

Example 1

Polymer beads were prepared which were imprinted with t-butoxycarbonyl -L-phenylalanine and contained magnetic iron oxide. The beads were prepared by a modification of the methods described in document 13 as explained below.

A suspension was formed containing t-butoxycarbonyl-L-phenylalanine (I mmol), methacrylic acid (4 mmol), 1,1,1-tris(hydroxymethyl)propanetrimethacrylate (4 mmol), 1,2-dichloroethane (3.5 g), 2,2'-azobis(2,4-dimethylvaleronitrile) (20 mg), magnetic iron oxide (<1 $\mu$m particles, supplied by BDH) (20 mg), and perfluorinated polymeric surfactant (prepared as described in document 13) (25 mg) in perfluoro-1,3-dimethylcyclohexane (20 ml) (saturated with 0.5 g 1,2-dichloroethane). The suspension was stirred at 600 rpm and 50° C. in a reactor as described in document 13 for 3 hours. Macroporous magnetically susceptible polymer beads having a molecular memory for the imprint molecule (i.e., the t-butoxycarbonyl-L-phenylalanine) of average diameter 18 $\mu$m resulted.

These beads were magnetic and could easily be separated from a solution by the application of a magnetic field. In order to verify that these beads retained the sought-for molecular memory recognition properties despite the presence of magnetically susceptible components within the beads, the following experiment was performed. The beads were washed in acetone, packed into a chromatographic column (100×4.6 mm), and washed further with methanol/acetic acid (7:3 v/v) (250 ml). HPLC studies were performed in dichloromethane containing acetic acid (1.0% v/v) at a flow rate of 0.5 ml/min. A racemic mixture of the two enantiomers of the chiral compound under invention (i.e., a mixture t-butoxycarbonyl-(D/L)-phenylalanine) was injected into the chromatographic column. The components were then detected by absorption at 254 nm. The chromatographic separation and resolution properties of these magnetically susceptible polymer beads were compared with those of beads prepared in exactly the same manner with the exception that they are not magnetically susceptible because the magnetic iron oxide component had been omitted from the suspension polymerization reactions. The results are shown below in the chart below.

|  | Plate No. | Void volume (ml) | $K'_D$ | $K'_L$ | α |
|---|---|---|---|---|---|
| Magnetic Polymer Beads | 489 | 1.70 | 2.12 | 5.39 | 2.54 |
| Nonmagnetic Polymer Beads | 464 | 1.78 | 2.02 | 5.28 | 2.62 |

In the above chart, $K'_D$ and $K'_L$ are the retention factors for t-butoxycarbonyl-D-phenylalanine and for t-butoxycarbonyl-L-phenylalanine, respectively, as calculated by standard chromatographic theory, and α is the separation factor (i.e., a measure of the polymer's ability to separate the imprint molecule from its enantiomer (i.e., to resolve the enantiomers forms of the chiral parent compound).

These results conclusively demonstrate that the experimentally-made beads described above:

(i) are magnetically susceptible;

(ii) possess specifically-tailored adsorptivities; and (iii) these adsorptivities are attributable to molecular memory recognition sites which were formed by molecular imprinting polymerization reactions.

Figure 6:
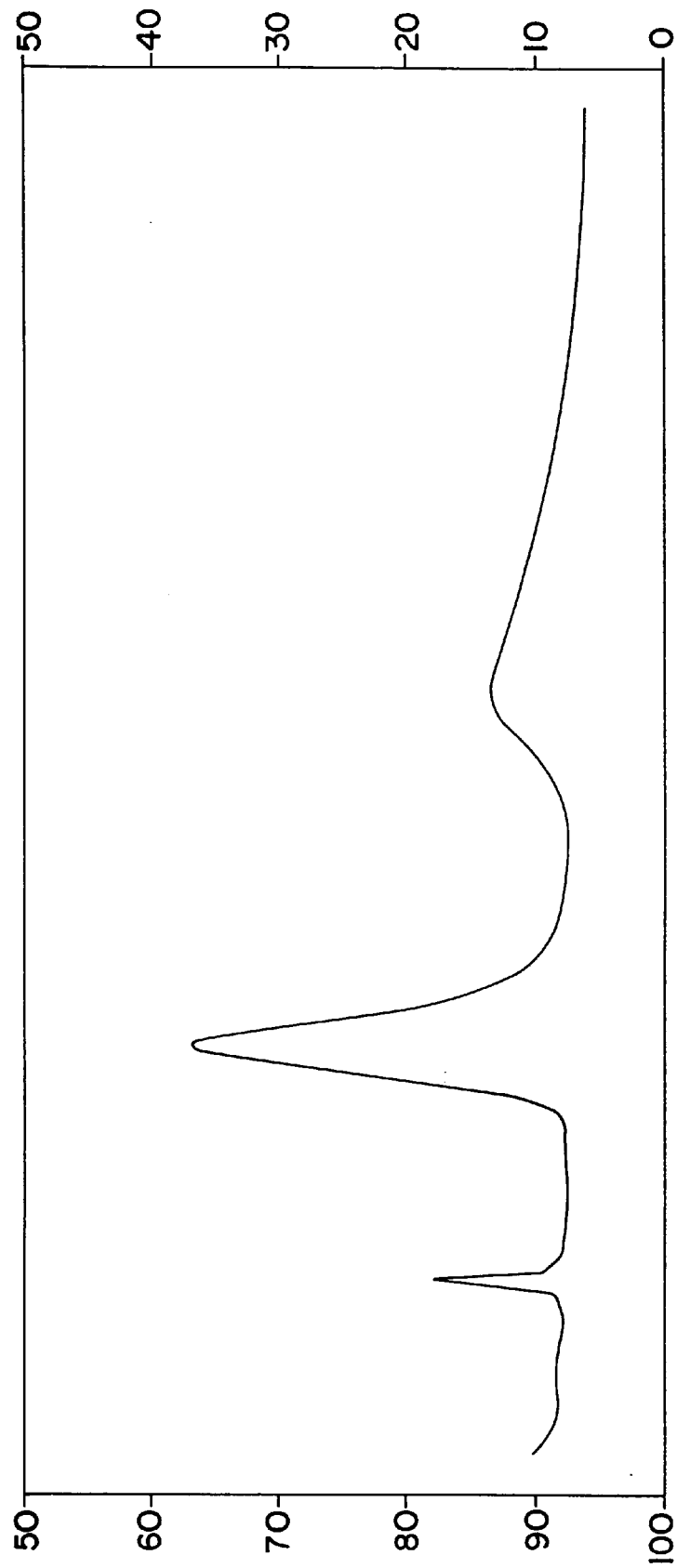
FIG. 6 depicts the chromatogram for the separation of the two different enantiomers of t-butoxycarbonyl-(D/L)-phenylalanine using the magnetically susceptible polymer particles prepared in Example 1.

FIG. 6 depicts the chromatogram for the separation and resolution of a mixture of t-butoxycarbonyl-(D/L)-phenylalanine using the magnetically susceptible beads of this example and as detailed in the first line of the above chart.

Figure 7:
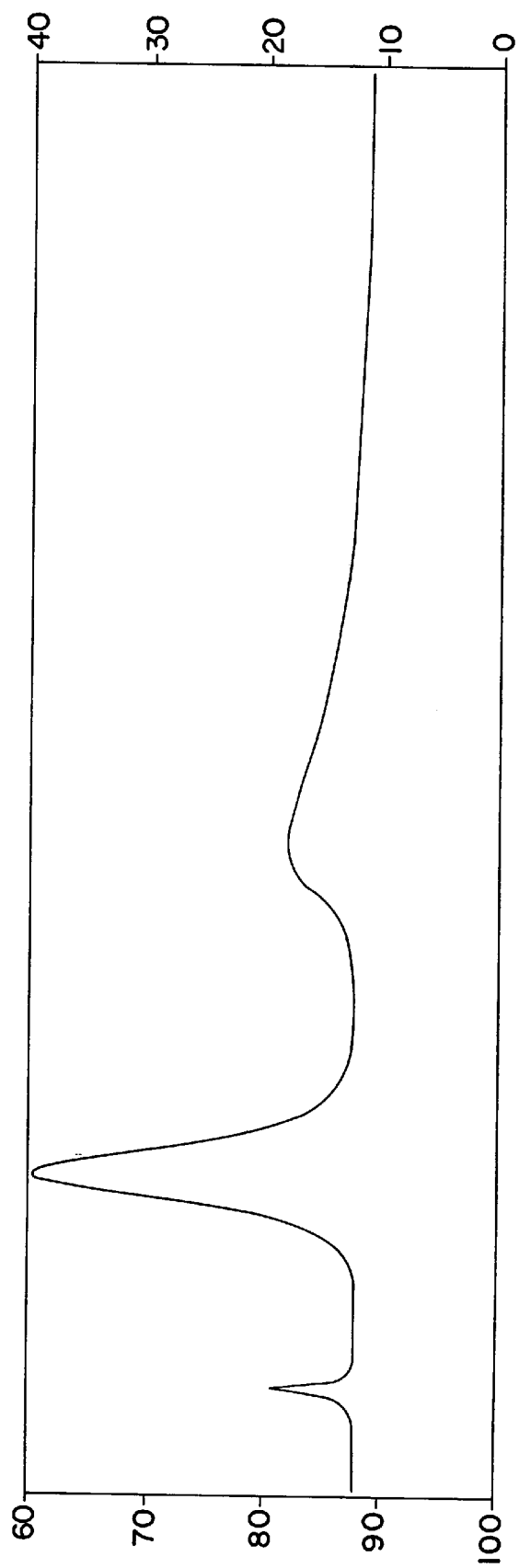
FIG. 7 depicts the chromatogram for the separation of the two different enantiomers of t-butoxycarbonyl-(D/L)-phenylalanine using the same polymer particles as prepared in Example 1 with the notable exception that the magnetic iron oxides were omitted from these polymer particles.

FIG. 7 depicts the chromatogram for the separation and resolution of a mixture of t-butoxycarbonyl-(D/L)-phenylalanine using the nonmagnetically susceptible particles of this example and as detailed in the second line of the above chart.

This example demonstrates the operability of (i) the magnetically susceptible polymer particles of the present invention and (ii) performing separations and/or resolutions of different enantiomers based upon the molecularly-imprinted memory recognition sites within these particles.

Example 2

A phenylalanine anilide imprinted polymer (1 g) was suspended in 5 ml of a solution containing 1.2 M $FeCl_2$ and 1.8 M $FeCl_3$. The suspension was sonicated for 3 minutes. After one hour it was centrifuged, the interstitial liquid was removed with a tissue paper, and the pellet was kept. The $FeCl_2/FeCl_3$ (both acqueous) -saturated imprinted particles were then resuspended in 5 ml ammonium hydroxide solution (56% $NH_4OH$) and sonicated for 3 minutes. The so formed black imprinted polymer particles containing magnetite inside the pores were finally washed with water until no more alkalinity could be detected in the supernatant. These particles exhibited magnetic susceptibility. The tailored-adsorptivities of these particles have not yet been experimentally investigated. However, based on the results in the prior example in combination with the entire disclosure of the present application, one of ordinary skill would be able to practice the alternative embodiments of the present invention without undue experimentation.

Although the present invention has been described in detail in the above specification, including particular references to specific embodiments and/or examples, a skilled artisan will clearly envision many alternatives and variations in light of the disclosure herein. Accordingly, the present invention is intended to cover all possible embodiments that fall within the spirit and scope of the appended claims. The full extent of the patent protection to which the invention is entitled is sought for in the present patent application.

Identification of Documents

1 U.S. Pat. No. 5,418,151 to Goodhue et al; issued May 23, 1995.

2 U.S. Pat. No. 4,335,094 to Mosbach; issued Jun. 15, 1982.

3 U.S. Pat. No. 4,115,534 to Ithakissios; issued Sep. 19, 1978.

4 U.S. Pat. No. 4,106,488 to Gordon; issued Aug. 15, 1978.

5 U.S. Pat. No. 3,985,649 to Eddelman; issued Oct. 12, 1976.

6 U.S. Pat. No. 3,970,518 to Giaver; issued Jul. 20, 1976

7 J. Org. Chem. Vol. 56, No. 1, 1991 pages 395–400.

8 PCT Application published on Jul. 17, 1986 as Intl. Pub. No. WO 86/04087.

9 Article by Gunter Wulff entitled The role of binding-site interactions in the molecular imprinting of polymers.

10 Marie Kempe, Ph.D. Thesis on Chiral Recognition (1994), University of Lund, Sweden ISBN No. 91-628-1253-X (see especially, Chapter 5 entitled: Polymer Systems in Non-Covalent Molecular Imprinting).

11 Pages 383–394 of Chapter 24 by Lars I. Anderson, Bjorn Ekberg, and Klaus Mosbach entitled Bioseparation and Catalysis in Molecularly Imprinted Polymers.

12 U.S. patent application Ser. No. (N/A) filed Aug. 21, 1995 by Klaus Mosbach, Mark T. Martin, and Richard J. Massey and entitled Separating Enantiomers by Molecular Imprinting Technology.

13 U.S. patent application Ser. No. 08/451,711 filed May 26, 1995 by Andrew G. Mayes and Klaus Mosbach and entitled Molecularly Imprinted Beaded Polymers and Stabilized Suspension Polymerization of the Same in Perfluorocarbon Liquids.

We claim:

1. Magnetically susceptible polymer particles, comprising (a) molecular memory recognition sites, and (b) magnetically susceptible components.

2. The particles of claim 1, wherein the magnetically susceptible components comprise one or more metal oxides.

3. The particles of claim 2, wherein the metal oxides are iron oxides or nickel oxides.

4. The particles of claim 2, wherein the metal oxides are iron oxides.

5. The particles of claim 2, wherein the metal oxides are nickel oxides.

6. Magnetically susceptible polymer particles, comprising the combination of
   (a) molecular memory recognition sites, and
   (b) magnetically susceptible components; said magnetically susceptible particles being prepared by the process comprising:
      (i) co-polymerizing one or more monomers and a cross-linking agent in the presence of at least one imprint molecule and at least one magnetically susceptible component; and
      (ii) removing the imprint molecule to form the molecular memory recognition sites.

7. The particles of claim 6, wherein the monomers are at least one of methacrylic acid, methyl methacrylate, benzyl methacrylate, or styrene.

8. The particles of claim 6, wherein the cross-linking agent is ethylene glycol dimethacrylate or 1,1,1-tris(hydroxymethyl)propane triacrylate.

9. Magnetically susceptible polymer particles, comprising the combination of molecular memory recognition sites and magnetically susceptible components, said magnetically susceptible polymer particles prepared by the process comprising:
   (a) co-polymerizing one or more monomers and a cross-linker agent in the presence of at least one imprint molecule to form a particle;
   (b) removing the imprint molecule from the particle, and
   (c) associating magnetically susceptible components with the particle.

10. The particles of claim 9 wherein the monomers are at least one of methacrylic acid, methyl methacrylate, benzyl methacrylate, or styrene.

11. The particles of claim 9, wherein the cross-linking agent is ethylene glycol dimethacrylate or 1,1,1-tris(hydroxymethyl)propane triacrylate.

12. A process for preparing magnetically susceptible polymer particles having molecular memory recognition sites, comprising polymerizing one or more monomers and a cross-linking agent in the presence of an imprint molecule and magnetically susceptible components and removing said imprint molecule to leave the molecular memory recognition site.

* * * * *